United States Patent [19]

Oswald et al.

[11] 3,969,517
[45] July 13, 1976

[54] ASYMMETRIC O,S-DIALKYL DITHIOPHOSPHORIC ACID ESTERS OF 1,2,3-BENZOTRIAZIN-4-ONES

[75] Inventors: Alexis A. Oswald, Mountainside; Paul L. Valint, Woodbridge, both of N.J.

[73] Assignee: Ciba-Geigy AG, Basel, Switzerland

[22] Filed: Jan. 29, 1975

[21] Appl. No.: 544,982

Related U.S. Application Data

[62] Division of Ser. No. 318,128, Dec. 26, 1972, Pat. No. 3,876,638.

[30] Foreign Application Priority Data

Dec. 23, 1971 Switzerland.................. 18827/71
Nov. 22, 1972 Switzerland.................. 17011/72

[52] U.S. Cl. ................................................ 424/200
[51] Int. Cl.² ........................................... A01N 9/36
[58] Field of Search ................ 260/248; 424/200

[56] References Cited
UNITED STATES PATENTS

| 3,131,186 | 4/1964 | Magee et al. | 424/200 |
| 3,202,658 | 8/1965 | Lorenz et al. | 424/200 |
| 3,294,631 | 12/1966 | Lorenz et al. | 424/200 |
| 3,309,371 | 3/1967 | Curry et al. | 424/200 |
| 3,325,492 | 6/1967 | Schrader et al. | 424/200 |
| 3,420,829 | 1/1969 | Lorenz et al. | 424/200 |
| 3,551,562 | 12/1970 | Rigterink | 424/200 |

*Primary Examiner*—Albert T. Meyers
*Assistant Examiner*—D. W. Robinson
*Attorney, Agent, or Firm*—Frederick H. Rabin

[57] ABSTRACT

Benztriazinonylmethyl-organophosphoric esters of the formula

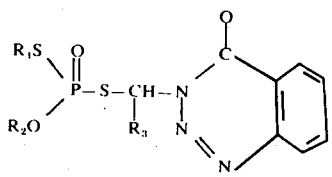

wherein $R_1$ represents ethyl, propyl, isopropyl, n-butyl, i-butyl or sec. butyl and $R_2$ represents methyl or ethyl, $R_3$ represents hydrogen or methyl, a process for their manufacture and their use in pest control.

5 Claims, No Drawings

ASYMMETRIC O,S-DIALKYL DITHIOPHOSPHORIC ACID ESTERS OF 1,2,3-BENZOTRIAZIN-4-ONES

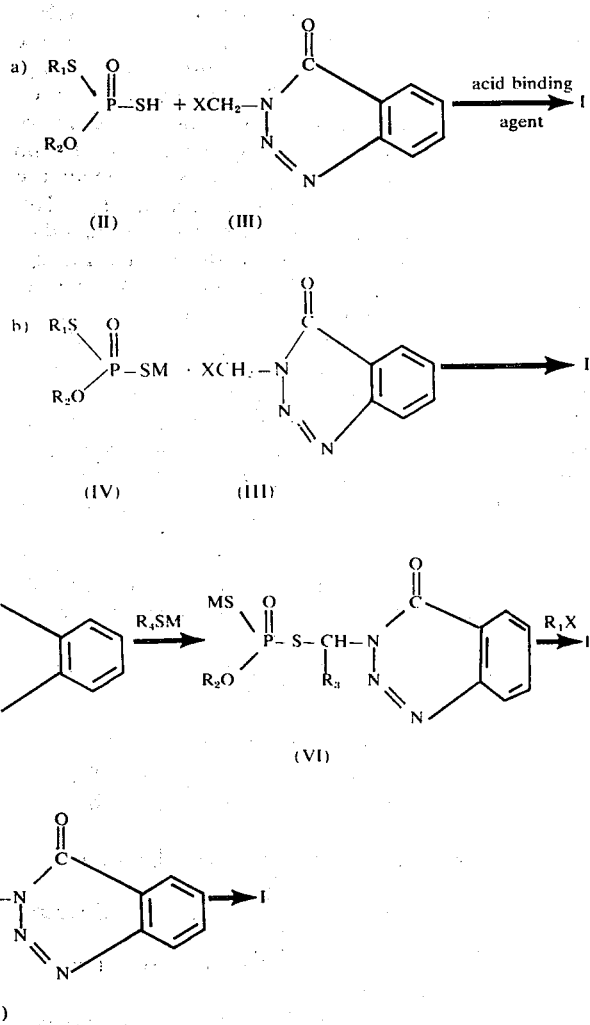

This is a division of application Ser. No. 318,128 filed on Dec. 26, 1972, now U.S. Pat. No. 3,876,638.

The present invention relates to benztriazinonylmethyl organophoshoric esters, a process for their manufacture and their use in pest control. The benztriazinonylmethyl organophosphoric esters have the formula

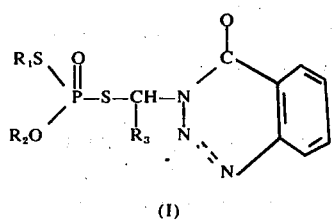

wherein $R_1$ represents ethyl, propyl, isopropyl, n-butyl, i-butyl or sec. butyl and $R_2$ represents methyl or ethyl, $R_3$ is hydrogen or methyl. Preferred compounds on account of their action are those of the formula I, wherein $R_1$ represents propyl and $R_2$ represents ethyl.

The compounds of the formula I can be manufactured by the following methods.

In the formulae II to VI, $R_1$ to $R_3$ have the meaning given for the formula I, X represents chlorine or bromine and M represents an alkali metal, in particular sodium or potassium, ammonium or alkylammonium with 1 to 5 carbon atoms, $R_4$ is hydrogen, $C_1$ to $C_4$ alkyl, $C_1$ to $C_4$ alkyl thiocarbamate group.

Suitable acid binding agents are: tertiary amines, e.g. trialkylamines, pyridine, dialkylanilines; inorganic bases, such as hydrides, hydroxides; carbonates and bicarbonates of alkali and alkaline earth metals. During the reactions it is sometimes necessary to use a catalyst, e.g. copper or cooper chloride.

Processes (a) to (d) can be carried out at normal pressure, at a temperature of −30° to 120°C., and in solvents or diluents.

Examples of suitable solvents or diluents are: ethers and ethereal compounds, such as diethyl ether, dipropyl ether, dioxan, tetrahydrofuran; amides, such as N,N-dialkylated carboxylic amides; aliphatic, aromatic and halogenated hydrocarbons, in particular benzene, toluene, xylene, chloroform, chlorobenzene; nitriles, such as acetonitrile; dimethyl sulphoxide; alcohols, such as ethanol; ketones, such as acetone, ethyl methyl ketone; and water.

The starting materials of the formula II to VII can be manufactured by methods analogous to those described in the literature.

The insecticidal action of analogous compounds is disclosed in the literature, but compared with these, the compounds of the formula I have surprisingly a lesser toxicity to warm blooded animals and a distinctly more powerful and long-lasting action against all development stages, such as eggs, larvae, nympjs, pupae and adults of insects, for example of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleriidae, Culicidae, Tipulidae, Stomoxydae, Muscidae, Caliphoridae, Trypetidae, Pulicidae.

The compounds of the formula I are also active against eggs, larvae and adults of representatives of the order Acarina, such as mites, spider mites and ticks, e.g. of the families Ixodidae, Argasidae, Tetranychidae and Demanyssidae.

By addition of other insecticides and/or acaricides it is possible to improve substantially the insecticidal or acaricidal action and to adapt it to given circumstances.

The following active substances are examples of suitable additives.

Organic phosphorus compounds

Bis-O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O-(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-(ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
o,o-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
o,o-dimethyl-O- p-nitrophenylthiophosphate (PARATHION-METHYL)
O,O-diethyl-O-p-nitrophenylthiophosphate (PARAHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4,5-trichlorophenylthiophosphate (RONNEL)
O-ethyl-O,2,4,5-trichlorophenylethylthiophosphate (TRICHLORONATE)
O,O-dimethyl-O- 2,5-dichloro-4-bromophenylthiophosphate (BROMOPHOS)
O,O-dimethyl-O-(2,5-dichloro-4-iodophenyl)-thiophosphate (JODOFENPHOS)
4-tert.butyl-2-chlorophenyl-N-methyl-O-methylamidophosphate (CRUFOMATE)
O,O-dimethyl-O-(3-methyl-4-methylmercaptophenyl)thiophosphate (FENTHION)
Isopropylamino-O-ethyl-O-(4-methylmercapto-3-methylphenyl)-phospate
O,O-diethyl-O-p-(methylsulphinyl)phenyl-thiophosphate (FENSULFOTHION)
O-p-(dimethylsulphamido)phenyl(FAMTHUR)
O,O,O', O-tetramethyl-O,O'-thiodi-p-phenylenethiophosphate
O-ethyl-S-phenyl-ethyldithiophosphate
O,O-dimethyl-O-(α-methylbenzyl-3-hydroxycrotonyl)phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxime-O,O-diethylthiophosphate (PHOXIM)
O,O-diethyl-O-(3-chloro-4-methyl-2-oxo-2-H-1-benzopyran-7-yl)-thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithiophosphate (PHOSALONE)
2-(diethoxyphosphinylimino)-1,3-dithiolane
O,O-dimethyl-S-[2-methoxy-1,3,4-thiadiazol-5-(4H)-onyl-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphate
O,O-diethyl-O-2-pyrazinylthiophosphate (THIONAZIN)
O,O-diethyl 2-isopropyl)-4-methyl-6-pyrimidyl)thiophosphate (DIAZINON)
O,O-diethyl-O-(2-quinoxalyl)thiophosphate
O,O-diethyl-S-(4-oxo-1,2,3-benzotriazin-3(4H)-ylmethyl)-dithiophosphate (AZINPHOS-METHYL)
O,O-diethyl-S-(4-oxo-1,2,3-benzotriazin-3(4H)-ylmethyl)-dithiophosphate (AZINPHOSETHYL)
S-[(4,6-diamino-s-triazin-2-yl)methyl]-O,O-dimethyldithiophosphate (MENAZON)
O,O-dimethyl-O-(3-chloro-4-nitrophenyl)thiophospate (CHLORTHION)
O,O-dimethyl-O(or S)-2-(ethylthioethyl)thiophosphate (DEMETON-S-METHYL)
2-(O,O-dimethyl-phosphoryl-thiomethyl)-5-methoxy-pyron-4-3,4-dichlorobenzyl-triphenyl-phosphoniumchloride O,O-diethyl-S-(2,5-dichlorophenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl 3-thiavaleramide (VAMIDOTHION)
O,O-dietyl-O-[2-dimethylamino-4-methylpyrimidyl-(6)]-thiophospate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetraapropyldithiophosphate
3-(dimethoxyphosphinyloxy)-N-methyl-N-methoxy-cis-crotonamide
O,O-dimethyl-S-(N-ethyllcarbamoylmethyl)dithiophosphate (ETHOATE-METHYL)
O,O-diethyl-S-(N-isopropyllcarbamoylmethyl) (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexametylphosphoric acid triamide (HEMPA)
O,O-dimethyl-O-(2-chloro-4-nitrophenyl)thiophosphate (DICAPTHON)
O,O-diethyl-O-p-cyanophenyl thiophosphate (CYANOX)
Omethyl-O-p-cyanophenylthiophosphonate
O,O-diethyl-O-2,4-dichlorophenylthiophosphate (DICHLORFENTHION)
O,2,4-dichlorophenyl-O-methylisopropylamidothiophosphate
O,O-diethyl-O-2,5-dichloro-4-bromophenylthiophosphate (BROMOPHOS-ETHYL)
dimethyl-p-(methylthio)phenylphosphate
O,O-dimethyl-O-p-sulphamidophenylthiophosphate
O-[p-(p-chlorophenyl)azophenyl]O,O-dimethylthiophosphate (AZOTHCATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyll-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O-(5-phenyl-3-isooxazolyl)thiophosphate
2-(diethoxyphosphinylimino)-4-methyl-1,3-dithiolane tris-(2-methyl-1-aziridinyl)-phosphine oxide (METEPA)
S-(2-chloro-1-phthalimidoethyl)-O,O-diethyldithiophosphate N-hydroxynaphthalimido-diethylphosphate
dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
diethyl-S-2-(ethylsulphinyl)ethyl dithiophosphate (OXIDISULFOTON)
bis-O,O-diethylthiophosphoric acid anhydride (SULFOTEP)
dimethyl-1,3-di(carbomethoxy)-1-propen-2-yl-phosphate
dimethyl-(2,2,2-trichloro-1-butyroyloxyethyl)phosphate (BUTONATE)
O,O-dimethyl-O-(2,2-dichloro-1-methoxy-vinyl)-phosphate
bis-(dimethylamido)fluorphosphate (DIMEFOX)
3,4-dichlorobenzyl-triphenylphosphoniumchloride
dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCABOPHENOTHION)
O,O-dimethyl-S-(ethylthiomethyl)dithiophosphate
diisopropylaminofluorophosphate (MIPAFOX)
O,O-dimethyl-S-(morpholinylcarbamoylmethyl)dithiophosphate (MORPHOTHION)
bismethylamido-phenylphosphate
O,O-dimethyl-S-(benzenesulphonyl)dithiophosphate
O,O-dimethyl-(S and O)-ethylsulphinylethylthiophosphate
O,O-diethyl-O-4-nitrophenylphosphate
triethoxy-isopropoxy-bis(thiophosphinyl)disulphide
2-methoxy-4H-1,3,2-benzodioxaphosphorin-2-oxide
octamethylpyrophosphoramide (SCHRADAN)
bis-(dimethoxythiophosphinylsulphido)-phenylmethane
N,N,N',N'-tetramethyldiamidofluorophosphate (DIMEFOX)
O-phenyl-O-p-nitrophenyl-methanethiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide
O,O-di-($\beta$-chloroethyl)-O-(3-chloro-4-methylcoumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2carbisopropoxyphenyl)-amidothiophosphate
5-(O,O-dimethylphosphoryl)-6-chloro-bicyclo(3.2.0)-heptadiene(1,5)

O-methyl-O-(2-i-propoxycarbonyl-1-methylvinyl)-ethylamidothiphosphate.

Nitrophenols and derivatives 4,6-dinitro-6-methylphenol, sodium salt [Dinitrocresol]
dinitrobutylphenol-(2,2',2")-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous pyrethin I
pyrethin II
3-allyl-2-methyl-4-oxo-2-cyclopentan-1-yl-chrysanthemumate (Allethrin)
6-chloropiperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxo-1,3-dithiolo-[4,5-b]-quinoxaline (Quinomethionate)
(I)-3-(2-furfuryl)-2-methyl-4-oxocyclopent-2-enyl-(I)-(cis+trans)chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbamyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorbenside]
2-thio-1,3-dithiolo-(5,6)-quinoxaline [Thiochinox]
prop-2-ynyl-(4-t-butylphenoxy)-cyclohexylsulphite [Propargil].

Formamidines 1-dimethyl-2-(2'-methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl-formamidine
1-n-butyl-2-(2'-methyl-4'-chlorophenyl-imino)-pyrolidine.

Urea

N-2-methyl-4-chlorophenyl-N',N'-dimethyl-thiourea.

Carbamates 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-(methylcarbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-O-(methylcarbamoyl)-oxime (ALDICARB)
8-quinaldyl-N-methylcarbamate and its salts methyl-2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
-m-tolyll-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate 3,4-dimethylphenyl-N-methylcarbamate
2-cyclopentylphenyl-N-methylcarbamate
3-dimethylamino-methyleneiminophenyl-N-methyl-carbamate (FORMETANATE) and its salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithiolane-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetal-carbamate
3-isopropylphenyl-N-methyl-N-methylthiomethyl-carbamate
O-(2,2-dimethyl-4-chloro-2,3-dihydro-7-benzofuranyl)-N-methylcarbamate
O-(2,2,4-trimethyl-2,3-dihydro-7-benzofuranyl)-N-methylcarbamate
O-naphthyl-N-methyl-N-acetal-carbamate
O-5,6,7,8-tetrahydronaphthyl
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-proparglyoxymethoxy
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-(α-methoxymethyl 2-propenyl)-phenyl-N-methyl-carbamate
2-chloro-5-tert.-phenyl-N-methyl-carbamate
4-(methyl-propargylamino-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonylethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons γ-hexachlorocyclohexane [GAMMEXANE; LINDAN; γ HCH]
1,2,4,5,6,7,8,8-octachloro-3α,4,7,7α'tetrahydro-4,7-methylene indane [CHLORDAN]
1,4,5,6,7,8,8-heptachloro,3α,4,7,7α-tetrahydro-4,7-methylene indane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8-,8α-octahydro-exo-1,4-endo-5,8-dimethanonaphthalene [DIFLORIN]
1,2,3,4,10,10-hexachloro-5,7-epoxy-1,4,4α,5,6,7,8-,8α-octyhydro-endo-endo-5,8-dimethanonaphthalene [ENDRIN]

In addition to the properties cited hereinabove, the compounds of the formula I also exhibit activity against representatives of the division Thallophyta. But they are also active against fungi, for example against the phytopathogenic fungi belonging to the following classes: Oomycetes, Zygomycetes, Ascomycetes, Basidiomycetes, Denteromycetes. The compounds of the formula I are also suitable for combating plant pathogenic nematodes.

The compounds of the formula I may be used as pure active substance or together with suitable carriers and-/or additives. Suitable carriers and additives can be solid or liquid and correspond to the substances conventionally used in formulation technique such, for example, as solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology. Mention may also be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms:

Solid forms:
Dusts, tracking agents, granules, coated granules, impregnated granules and homogeneous granules.

Liquid forms:
a. active substances which are dispersible in water: wettable powders, pasts, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminum silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilise the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilise the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove in such a manner that, the size of the solid particles does not exceed 0.02 to 0.04 $\mu$ in wettable powders, and 0.03 $\mu$ in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions which boil between 120° and 350°C. The solvents must be practically odourless, not phytotoxic, and inert to the active substances.

Furthermore, the agents according to the invention can be applied in the form of solutions. For this purpose the active substances, or several active substances of the general formula I, are dissolved in suitable organic solvents, mixtures of solvents or in water. Aliphatic and aromatic hydrocarbons, chlorinated derivatives thereof, alkyl naphthalenes, and mineral oils, singly or in admixture with each other, can be used as organic solvents.

The content of active substance in the above described agents is between 0.1 to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:

a. 5 parts of active substance
   95 parts of talcum
b. 2 parts of active substance
   1 part of highly disperse silicic acid
   97 parts of talcum.

The active substances are mixed with the carriers and ground.

Granules

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with ephichlorohydrin and dissolved with 6 parts of acetone; the polyethylene glycol and cetyl polyglycol ether are then added. The thus obtained solution is sprayed on kaolin, and the acetone subsequently evaporated in vacuo.

Wettable powder

The following constituents are used for the preparation of (a) a 40%, (b) and (c) a 25%, and (d) a 10% wettable powder:

a. 40 parts of active substance,
   5 parts of sodium lignin sulphonate,
   1 part of sodium dibutyl-naphthalene sulphonate,
   54 parts of silicic acid.
b. 25 parts of active substance,
   4.5 parts of calcium lignin sulphonate,
   1.9 parts of Champagne chalk/hydroxyethyl cellulose mixture (1:1),
   1.5 parts of sodium dibutyl naphthalene sulphonate,
   19.5 parts of silicic acid,
   19.5 parts of Champagne chalk,
   28.1 parts of kaolin.
c. 25 parts of active substance,
   12.5 parts of isooctylphenoxy-polyoxyethylene-ethanol,
   1.7 parts of Champagne chalk/hydroxyethyl cellulose mixture (1:1),
   8.3 parts of sodium aluminium silicate,
   16.5 parts of kieselguhr,
   46 parts of kaolin.
d. 10 parts of active substance,
   3 parts of a mixture of the sodium salts of saturated fatty alcohol sulphates,
   5 parts of naphthalenesulphonic acid-formaldehyde condensate,
   82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:

a. 10 parts of active substance,
   3.4 parts of epoxidised vegetable oil,
   13.4 parts of a combination emulsifier consisting of fatty alcohol polyglycol ether and alkylarylsulphonate calcium salt,
   40 parts of dimethylformamide,
   43.2 parts of xylene,
b. 25 parts of active substance,
   2.5 parts of epoxidised vegetable oil,
   10 parts of an alkylarylsulphonate/fatty alcohol-polyglycol ether mixture
   5 parts of dimethylformamide,
   57.5 parts of xylene.

From these concentrates it is possible to produce, by dilution with water, emulsions of any desired concentration.

Spray

The following constituents are used to prepare a 5% spray:

5 parts of active substance,
1 part of ephichlorohydrin,
94 parts of benzine (boilimg limits 160°–190°C).

EXAMPLE 1

O-ethyl-S-n-butyl-S-(3,4-dihydro-4-1,2,3-benzotriazinon-3-yl methyl)-dithiophosphate 11.3 g of N-chloromethylbenzazimide and 15 g of the potassium salt of O-ethyl-S-n-butyldithiophosphoric acid are suspended in 100 ml of acetone at room temperature. The reaction mixture is stirred for 1 hour at room temperature and for 5 hours at 55°0: it is then cooled and stirred with 300 ml of ice water. The precipitated oil is taken up in 100 ml of benzene. The benzene layer is separated, washed with 3% $Na_2CO_3$ solution and with water and subsequently dried with sodium sulphate. The benzene is distilled off to lavae as residue 15 g of an oil product with a refractive index of $n_D^{24}$ = 1.5819; $N_D^{25}$ = 1.5817.

| Analysis for $C_{14}H_{20}N_3P_3PS_2$ | calculated | found |
|---|---|---|
| % P | 8.3 | 8.5 |
| % N | 11.25 | 10.8 |

The following compounds are manufactured in analogous manner:

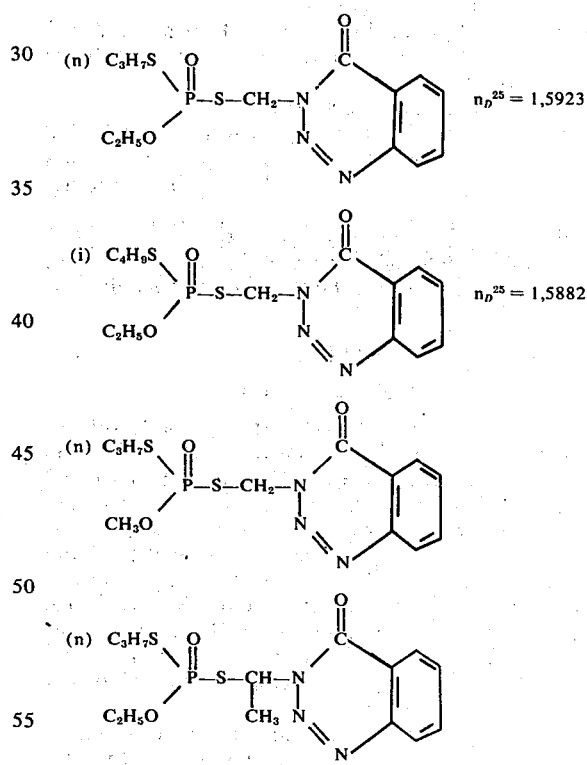

EXAMPLE 2

Insecticidal ingest poison action

Cotton plants were sprayed with a 0.05% aqueous active substance emulsion (obtained from a 10% emulsifiable concentrate).

After the spray coating had dried, the cotton plants were populated with Spodoptera littoralis or Heliothis virescens larvae ($L_3$). The test was carried out at 24C and 60% relative humidity.

15

In the above test, the compounds according to Example 1 displayed good insecticidal ingest poison action against Spodoptera and Heliothis larvae.

EXAMPLE 3

Action against *Chilo suppressalis*

Six rice plants at a time of the variety Caloro were transplanted in plasticpots (diameter at the top = 17 cm) and reared to a height of about 60 cm. Infestation with *Chilo suppressalis* larvae ($L_1$, 3–4 mm in length) took place 2 days after the active substance had been applied in granule form to the paddy water (rate of application: 8 kg of active substance per hectare). Evaluation of the insecticidal action ensued 10 days after application of the granules.

In the above test, the compounds according to Example 1 acted against *Chilo suppressalis*.

EXAMPLE 4

Action against ticks

A. *Rhipicephalus bursa*

Five adult ticks or 50 tick larvae were counted into a test tube and immersed for 1 to 2 minutes in 2 ml of an aqueous emulsion series each containing 100, 10, 1 and 0.1 ppm of test substance. The tube was then sealed with a standardised cotton wool plug and stood on its head so as to enable the cotton wool to absorb the active substance emulsion.

In the case of the adults evaluation took place after 2 weeks, and in that of the larvae after 2 days. Each test was repeated twice.

B. *Boophilus microplus* (larvae)

Test were carried out with 20 sensitive and 20 OP resistant larvae with a dilution series analogous to that used in test A. (The resistance refers to the tolerability of diazinon).

In these tests, the compound according to Example 1 acted against adults and larvae of *Rhipicephalus bursa* and sensitive and OP-resistant larvae of *Boophilus microplus*.

EXAMPLE 5

Acaricidal action

*Phaseolus vulgaris* (plants) were overlaid with an infested piece of leaf from a mass culture of *Tetranychus urticae* 12 hours before the test for acaricidal action. The mobile stages which had spread over the plants were sprayed with the emulsified test preparations from a chromatography atomiser so that the spray broth did not run off. The number of living and dead larvae, adults and eggs were evaluated after 2 to 7 days under a stereoscopic microscope and the reuslt was expressed in percentages. During the "interim", the treated plants were kept in greenhouse compartments at 25°C.

In the above test, the compounds according to Example 1 acted against adults larvae and eggs of *Tetranychus urticae*.

EXAMPLE 6

Action against soil nematodes

To test the action against soil nematodes, the active substances were applied to, and intimately mixed with, soil infected with root gall nematodes (*Meloidgyne arenaria*), in the specifically indicated concentrations. Immediately afterwards, tomato cuttings were planted in the thus prepared soil in a series of tests, and after a waiting time of 8 days tomato seeds were sown in another test series.

16

In order to assess the nematocidal action, the galls present on the roots were counted 28 days after planting and sowing respectively.

In this test, the active substances according to Example 1 display good action against *Meloidgyne arenaria*.

What is claimed is:

1. An insecticidal and acaricidal composition comprising (1) an insecticidally or acaricidally effective amount of a compound of the formula

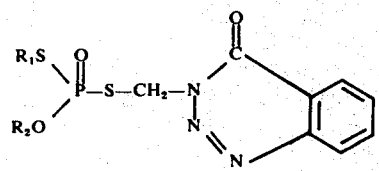

wherein $R_1$ is N-propyl, isopropyl, n-butyl, isobutyl or sec-butyl, and $R_2$ is methyl or ethyl, and (2) a suitable carrier.

2. A method for combatting insects and acarids which comprises applying thereto an insecticidally or acaricidally effective amount of a compound of the formula

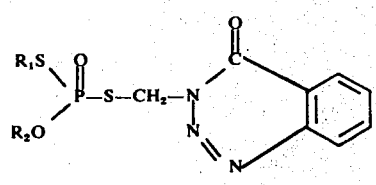

wherein $R_1$ represents n-propyl, isopropyl, n-butyl, isobutyl or sec-butyl, and $R_2$ represents methyl or ethyl.

3. The method according to claim 2 in which the compound is

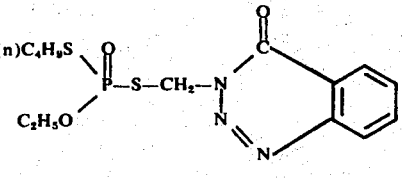

4. The method according to claim 2 in which the compound is

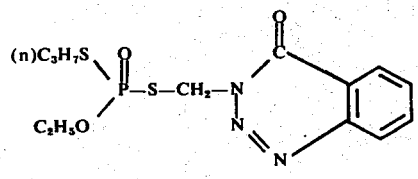

5. The method according to claim 2 in which the compound is

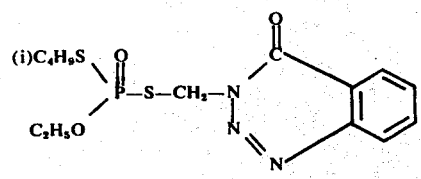

* * * * *